(12) United States Patent
Orphanos et al.

(10) Patent No.: US 12,357,285 B2
(45) Date of Patent: Jul. 15, 2025

(54) UNITARY DEVICE FOR VESSEL HARVESTING AND METHOD OF USING SAME

(71) Applicant: Saphena Medical, Inc., West Bridgewater, MA (US)

(72) Inventors: Mark Orphanos, Foxboro, MA (US); Michael Glennon, Norwell, MA (US)

(73) Assignee: Saphena Medical, Inc., West Bridgewater, MA (US)

( * ) Notice: Subject to any disclaimer, the term of this patent is extended or adjusted under 35 U.S.C. 154(b) by 0 days.

(21) Appl. No.: 16/839,542

(22) Filed: Apr. 3, 2020

(65) Prior Publication Data

US 2020/0315650 A1 Oct. 8, 2020

Related U.S. Application Data

(60) Provisional application No. 62/829,990, filed on Apr. 5, 2019.

(51) Int. Cl.
*A61B 17/00* (2006.01)
*A61B 1/00* (2006.01)
(Continued)

(52) U.S. Cl.
CPC .... *A61B 17/00008* (2013.01); *A61B 1/00006* (2013.01); *A61B 1/000094* (2022.02);
(Continued)

(58) Field of Classification Search
CPC ...... A61B 17/320016; A61B 17/32002; A61B 1/00006; A61B 1/00009; A61B 1/00016; A61B 1/00018; A61B 1/00064; A61B 1/00066; A61B 1/0684; A61B 2017/00221; A61B 2017/00734; A61B 2017/00778;
(Continued)

(56) References Cited

U.S. PATENT DOCUMENTS

| 4,357,940 A | 11/1982 | Muller |
| 5,185,006 A | 2/1993 | Williamitis et al. |

(Continued)

FOREIGN PATENT DOCUMENTS

| AU | 2007203086 A1 | 1/2009 |
| EP | 1120129 A1 | 8/2001 |

(Continued)

OTHER PUBLICATIONS

International Search Report and Written Opinion in corresponding International Patent Application No. PCT/US2020/026594, mailed Jun. 19, 2020 (14 pages).

(Continued)

*Primary Examiner* — Ryan N Henderson
*Assistant Examiner* — Pamela F Wu
(74) *Attorney, Agent, or Firm* — SCHWEGMAN LUNDBERG & WOESSNER, P.A.

(57) ABSTRACT

Unitary vessel harvesting devices with integrated components is provided. In some embodiments, such devices comprise an elongated body having a proximal end and a distal end, a dissection tip disposed at the distal end of the elongated body. The dissection tip can include integrated circuitry to provide an in-tip camera, lighting and data communications.

20 Claims, 10 Drawing Sheets

(51) Int. Cl.
  *A61B 1/05* (2006.01)
  *A61B 1/06* (2006.01)
  *A61B 17/32* (2006.01)

(52) U.S. Cl.
  CPC ...... *A61B 1/00016* (2013.01); *A61B 1/00018* (2013.01); *A61B 1/00064* (2013.01); *A61B 1/05* (2013.01); *A61B 1/0684* (2013.01); *A61B 17/320016* (2013.01); *A61B 2017/00221* (2013.01); *A61B 2017/0023* (2013.01); *A61B 2017/00734* (2013.01); *A61B 2017/00778* (2013.01)

(58) Field of Classification Search
  CPC .............. A61B 1/0008; A61B 1/00087; A61B 1/00027; A61B 1/00029; A61B 1/00032; A61B 1/00034; A61B 1/04; A61B 1/00114; A61B 1/0655; A61B 1/0676; A61B 1/05–053; A61B 1/0027–000341; A61B 1/00096–00097
  USPC .......................... 600/101, 104–106, 109, 183
  See application file for complete search history.

(56) References Cited

U.S. PATENT DOCUMENTS

| | | | |
|---|---|---|---|
| 5,209,749 A | 5/1993 | Buelna | |
| 5,350,391 A | 9/1994 | Iacovelli | |
| 5,373,840 A | 12/1994 | Knighton | |
| 5,556,408 A | 9/1996 | Farhat | |
| 5,591,183 A | 1/1997 | Chin | |
| 5,601,581 A | 2/1997 | Fogarty et al. | |
| 5,676,636 A | 10/1997 | Chin | |
| 5,695,514 A | 12/1997 | Chin | |
| 5,702,813 A | 12/1997 | Murata et al. | |
| 5,728,123 A | 3/1998 | Lemelson et al. | |
| 5,772,576 A | 6/1998 | Knighton et al. | |
| 5,797,946 A | 8/1998 | Chin | |
| 5,810,805 A | 9/1998 | Sutcu et al. | |
| 5,823,946 A | 10/1998 | Chin | |
| 5,873,889 A | 2/1999 | Chin | |
| 5,891,141 A | 4/1999 | Rydell | |
| 5,895,353 A | 4/1999 | Lunsford et al. | |
| 5,916,233 A | 6/1999 | Chin | |
| 5,921,919 A | 7/1999 | Chin et al. | |
| 5,941,819 A | 8/1999 | Chin | |
| 5,968,065 A | 10/1999 | Chin | |
| 5,976,168 A | 11/1999 | Chin | |
| 5,980,549 A | 11/1999 | Chin | |
| 5,984,937 A | 11/1999 | Morse et al. | |
| 5,993,378 A * | 11/1999 | Lemelson .......... | A61B 1/00096 600/109 |
| 5,993,384 A | 11/1999 | Lunsford et al. | |
| 6,019,771 A | 2/2000 | Bennett et al. | |
| 6,030,406 A | 2/2000 | Davis et al. | |
| 6,036,714 A | 3/2000 | Chin | |
| 6,042,538 A | 3/2000 | Puskas | |
| 6,102,909 A | 8/2000 | Chen et al. | |
| 6,162,173 A | 12/2000 | Chin et al. | |
| 6,176,825 B1 | 1/2001 | Chin et al. | |
| 6,203,557 B1 | 3/2001 | Chin | |
| 6,203,559 B1 | 3/2001 | Davis et al. | |
| 6,264,670 B1 | 7/2001 | Chin | |
| 6,277,137 B1 | 8/2001 | Chin | |
| 6,287,304 B1 | 9/2001 | Eggers et al. | |
| 6,348,037 B1 | 2/2002 | Chin et al. | |
| 6,402,720 B1 | 6/2002 | Miller et al. | |
| 6,406,425 B1 | 6/2002 | Chin et al. | |
| 6,428,468 B1 | 8/2002 | Knighton et al. | |
| 6,428,539 B1 | 8/2002 | Baxter et al. | |
| 6,428,556 B1 | 8/2002 | Chin | |
| 6,432,044 B1 | 8/2002 | Lunsford et al. | |
| 6,471,638 B1 | 10/2002 | Chang et al. | |
| 6,506,200 B1 | 1/2003 | Chin | |
| 6,527,771 B1 | 3/2003 | Weadock | |
| 6,569,082 B1 | 5/2003 | Chin | |
| 6,607,547 B1 | 8/2003 | Chin | |
| 6,673,087 B1 | 1/2004 | Chang et al. | |
| 6,702,813 B1 | 3/2004 | Baxter et al. | |
| 6,706,052 B1 | 3/2004 | Chin | |
| 6,749,609 B1 | 6/2004 | Lunsford et al. | |
| 6,752,756 B2 | 6/2004 | Lunsford et al. | |
| 6,811,546 B1 | 11/2004 | Callas et al. | |
| 6,814,696 B1 | 11/2004 | Chang et al. | |
| 6,830,546 B1 | 12/2004 | Chin et al. | |
| 6,951,568 B1 | 10/2005 | Chin | |
| 6,976,957 B1 | 12/2005 | Chin et al. | |
| 6,979,290 B2 | 12/2005 | Mourlas et al. | |
| 7,001,404 B1 | 2/2006 | Chin | |
| 7,033,357 B2 | 4/2006 | Baxter et al. | |
| 7,066,875 B2 | 6/2006 | Knighton et al. | |
| 7,214,180 B2 | 5/2007 | Chin | |
| 7,264,587 B2 | 9/2007 | Chin | |
| 7,276,075 B1 | 10/2007 | Callas et al. | |
| 7,326,178 B1 | 2/2008 | Lunsford et al. | |
| 7,344,536 B1 | 3/2008 | Lunsford et al. | |
| 7,384,423 B1 | 6/2008 | Chin | |
| 7,384,723 B2 | 6/2008 | Kakuta et al. | |
| 7,398,781 B1 | 7/2008 | Chin | |
| 7,476,198 B1 | 1/2009 | Chin et al. | |
| 7,485,092 B1 | 2/2009 | Stewart et al. | |
| 7,534,243 B1 | 5/2009 | Chin et al. | |
| 7,544,195 B2 | 6/2009 | Lunsford et al. | |
| 7,556,633 B2 | 7/2009 | Lindsay | |
| 7,645,289 B2 | 1/2010 | Bayer | |
| 7,695,470 B1 | 4/2010 | Stewart et al. | |
| 7,867,163 B2 | 1/2011 | Chin et al. | |
| 7,887,558 B2 | 2/2011 | Lin et al. | |
| 7,918,848 B2 | 4/2011 | Lau et al. | |
| 7,931,590 B2 | 4/2011 | Willis | |
| 7,938,842 B1 | 5/2011 | Chin | |
| 7,972,265 B1 | 7/2011 | Chin et al. | |
| 7,981,133 B2 | 7/2011 | Chin | |
| 8,075,559 B2 | 12/2011 | Stewart et al. | |
| 8,083,664 B2 | 12/2011 | Davis | |
| 8,097,010 B2 | 1/2012 | Kasahara et al. | |
| 8,197,472 B2 | 6/2012 | Lau et al. | |
| 8,241,210 B2 | 8/2012 | Lunsford et al. | |
| 8,372,096 B2 | 2/2013 | Kadykowski et al. | |
| 8,414,480 B2 | 4/2013 | Kendale et al. | |
| 8,460,331 B2 | 6/2013 | Chin | |
| 8,623,003 B2 | 1/2014 | Lau et al. | |
| 8,657,818 B2 | 2/2014 | Lin | |
| 8,676,636 B2 | 3/2014 | Genschel et al. | |
| 9,119,900 B2 | 9/2015 | Chin | |
| 9,498,246 B2 | 11/2016 | Chin et al. | |
| 9,730,782 B2 | 8/2017 | Stewart | |
| 9,798,246 B2 | 10/2017 | Streefkerk et al. | |
| 9,814,481 B2 | 11/2017 | Orphanos et al. | |
| 9,943,328 B2 | 4/2018 | Orphanos et al. | |
| 10,363,056 B2 | 7/2019 | Orphanos | |
| 10,537,353 B2 | 1/2020 | Chin | |
| 10,874,415 B2 | 12/2020 | Orphanos | |
| 11,751,896 B2 | 9/2023 | Orphanos et al. | |
| 2003/0032863 A1* | 2/2003 | Kazakevich ....... | A61B 1/00105 600/173 |
| 2003/0229366 A1 | 12/2003 | Reggie et al. | |
| 2004/0133228 A1 | 7/2004 | Bayer | |
| 2004/0147909 A1 | 7/2004 | Johnston | |
| 2004/0158143 A1 | 8/2004 | Flaherty et al. | |
| 2004/0204725 A1 | 10/2004 | Bayer | |
| 2004/0243167 A1 | 12/2004 | Tanaka et al. | |
| 2005/0154262 A1 | 7/2005 | Banik | |
| 2005/0159764 A1 | 7/2005 | Kasahara | |
| 2005/0192613 A1 | 9/2005 | Lindsay | |
| 2005/0272975 A1 | 12/2005 | McWeeney | |
| 2006/0094930 A1* | 5/2006 | Sparks ........... | A61B 17/320783 600/104 |
| 2006/0095056 A1 | 5/2006 | Douglas et al. | |
| 2006/0271032 A1 | 11/2006 | Chin | |
| 2006/0271038 A1 | 11/2006 | Johnson et al. | |
| 2006/0271082 A1 | 11/2006 | Kirchhevel et al. | |
| 2007/0016183 A1 | 1/2007 | Lee et al. | |

(56) References Cited

U.S. PATENT DOCUMENTS

| | | |
|---|---|---|
| 2007/0142711 A1* | 6/2007 | Bayer ............... A61B 1/00101 600/172 |
| 2007/0225556 A1 | 9/2007 | Ortiz et al. |
| 2008/0195128 A1* | 8/2008 | Orbay ............... A61B 1/00052 606/170 |
| 2008/0208192 A1 | 8/2008 | Kadykowski |
| 2008/0255419 A1 | 10/2008 | Kendale et al. |
| 2008/0306335 A1 | 12/2008 | Lau et al. |
| 2009/0023986 A1 | 1/2009 | Stewart |
| 2009/0048486 A1* | 2/2009 | Surti ................... A61B 1/0008 600/127 |
| 2009/0079819 A1* | 3/2009 | Abe .................. A61B 1/00016 348/E7.085 |
| 2009/0105538 A1* | 4/2009 | Van Dam ........... A61B 1/00105 345/173 |
| 2009/0299144 A1 | 12/2009 | Shigemori et al. |
| 2009/0318758 A1 | 12/2009 | Farr et al. |
| 2010/0022824 A1* | 1/2010 | Cybulski ............... A61B 1/051 600/104 |
| 2010/0191057 A1 | 7/2010 | Jansen et al. |
| 2010/0198009 A1 | 8/2010 | Farr et al. |
| 2010/0268175 A1 | 10/2010 | Lunsford et al. |
| 2010/0292533 A1 | 11/2010 | Kasahara |
| 2011/0009694 A1* | 1/2011 | Schultz ................ A61B 1/317 600/109 |
| 2011/0046624 A1 | 2/2011 | Lin |
| 2011/0295072 A1 | 12/2011 | Boulais et al. |
| 2012/0149983 A1 | 6/2012 | Chin |
| 2012/0209074 A1 | 8/2012 | Titus |
| 2012/0232342 A1 | 9/2012 | Reydel |
| 2012/0289957 A1 | 11/2012 | Emmerich |
| 2013/0046138 A1 | 2/2013 | McLawhorn |
| 2013/0144276 A1 | 6/2013 | Crisostomo et al. |
| 2013/0165746 A1 | 6/2013 | Chin |
| 2013/0197299 A1 | 8/2013 | Chin |
| 2013/0274548 A1 | 10/2013 | Fels et al. |
| 2014/0296847 A1 | 10/2014 | Chin et al. |
| 2014/0364691 A1 | 12/2014 | Krivopisk et al. |
| 2014/0378957 A1* | 12/2014 | Orphanos .......... A61B 18/1482 606/171 |
| 2015/0005580 A1 | 1/2015 | Petersen |
| 2015/0141938 A1 | 5/2015 | Pravongviengkham et al. |
| 2015/0316046 A1 | 11/2015 | Kang et al. |
| 2016/0174810 A1* | 6/2016 | Dresher ............ A61B 1/00009 600/109 |
| 2016/0174814 A1* | 6/2016 | Igov ................. A61B 1/00101 600/106 |
| 2016/0192822 A1* | 7/2016 | Ofir ..................... A61B 1/0011 600/129 |
| 2016/0317171 A1 | 11/2016 | Orphanos |
| 2016/0367279 A1 | 12/2016 | Orphanos et al. |
| 2017/0020546 A1 | 1/2017 | Chin et al. |
| 2017/0035487 A1 | 2/2017 | Kadykowski et al. |
| 2017/0188794 A1 | 7/2017 | Ouyang et al. |
| 2017/0354433 A1 | 12/2017 | Nickson |
| 2018/0028213 A1 | 2/2018 | Orphanos et al. |
| 2019/0076161 A1 | 3/2019 | Chin et al. |
| 2019/0343547 A1 | 11/2019 | Orphanos et al. |
| 2020/0113418 A1* | 4/2020 | Levy ................. A61B 1/00096 |
| 2020/0315650 A1 | 10/2020 | Orphanos et al. |
| 2020/0345408 A1 | 11/2020 | Orphanos et al. |
| 2023/0404611 A1 | 12/2023 | Orphanos et al. |
| 2024/0148399 A1 | 5/2024 | Orphanos et al. |
| 2024/0148400 A1 | 5/2024 | Orphanos et al. |

FOREIGN PATENT DOCUMENTS

| | | |
|---|---|---|
| EP | 1570787 A1 | 9/2005 |
| EP | 1935349 A2 | 6/2008 |
| EP | 2364653 A1 | 9/2011 |
| JP | H03064603 U | 6/1991 |
| JP | 7178108 H | 7/1995 |
| JP | 7184846 H | 7/1995 |
| JP | 2000217924 A | 8/2000 |
| JP | 2002543893 A | 12/2002 |
| JP | 2003500152 A | 1/2003 |
| JP | 2003190171 A | 7/2003 |
| JP | 2005538753 A | 12/2005 |
| JP | 2009519109 A | 5/2009 |
| JP | 2010534531 A | 11/2010 |
| JP | 2012511357 A | 5/2012 |
| JP | 2012147968 A | 8/2012 |
| JP | 2016209549 A | 12/2016 |
| JP | 2019507628 A | 3/2019 |
| WO | 2000067828 A1 | 11/2000 |
| WO | 2002001998 A2 | 1/2002 |
| WO | 2003013367 A2 | 2/2003 |
| WO | 2004043530 A1 | 5/2004 |
| WO | 2006127241 A2 | 11/2006 |
| WO | 2009015396 A2 | 1/2009 |
| WO | 2009148809 A1 | 12/2009 |
| WO | 2011130399 A1 | 10/2011 |
| WO | 2014158613 A1 | 10/2014 |
| WO | 2017147001 A1 | 8/2017 |

OTHER PUBLICATIONS

Extended European Search Report issued in European Application No. 20799040.9 mailed Dec. 22, 2022.

International Search Report and Written Opinion dated Mar. 6, 2024 in corresponding International Patent Application No. PCT/US2023/036675 (18 pages).

* cited by examiner

UNITARY DEVICE FOR VESSEL HARVESTING AND METHOD OF USING SAME

CROSS-REFERENCE TO RELATED APPLICATION(S)

This application claims priority to, and the benefit of, U.S. Provisional Application No. 62/829,990, filed Apr. 5, 2019, for all subject matter common to both applications. The disclosure of said provisional application is hereby incorporated by reference in its entirety.

FIELD OF THE INVENTION

The present disclosure relates to a vessel harvesting device. In particular, the present disclosure relates to a disposable vessel harvesting device with integrated visualization and lighting features.

BACKGROUND

Generally, current EVH devices can be supplemented with additional components and their respective associated systems for performing different procedures. In some implementations, for example, EVH devices can be configured to receive a reusable rigid endoscope within a cannula of the EVH device. Similarly, conventional EVH devices can be configured to couple with a reusable camera and independent light source. Traditionally, the reusable camera can be coupled to a proximal end of the rigid endoscope. The EVH device and each reusable component can each include their own independent power and communication cords communicating with separate processing components located outside of a sterile field. For example, the reusable camera can have a power/video cable plugged into a camera processor. The camera processor processes the image data from the camera and displays it on a monitor attached to the camera processor. It is also common to have fiberoptic light cord attached to the endoscope, which can be attached to a separate light source to deliver light down the cord, down the scope to the distal tip of the EVH device.

Configurations for conventional EVH devices have a number of drawbacks. For example, each reusable component for use with an EVH device has to be individually sterilized prior to use with the EVH device within a sterile field. This requires significant time and risks if any of the reusable components is not properly sterilized. Additionally, having multiple separate systems with separate power/communication cords adds bulk, movement restrictions, etc. to the EVH device which can make the device more difficult to use.

SUMMARY

There is a need for improvements for EVH devices. The present disclosure is directed toward further solutions to address this need, in addition to having other desirable characteristics. Specifically, the present disclosure is directed to a disposable vessel harvesting device with integrated illumination and visualization components.

In accordance with example embodiments of the present invention, a surgical device is provided. The surgical device includes an elongated body having disposed, at its distal end, a tip that can minimize trauma to surrounding tissue during its advancement and an integrated circuit located within the tip, the integrated circuit having an imaging device, an illumination source, and communication circuitry. The surgical device also includes a single cable connecting the communication circuitry of the integrated circuit to a processing tower remotely situated from the elongated body, the single cable providing power and data lines to the surgical device, imaging device, and the illumination source.

In accordance with aspects of the present invention, the surgical device further includes a cutting unit. The integrated circuit can further include at least one light emitting diode. The integrated circuit can further include a battery. The communication circuitry can include a wireless transceiver. The integrated circuit can receive power from the battery and exchanges data via the wireless transceiver. The communication circuitry can include at least one of a conductive line and an optical line The conductive line can include small gauge wiring extending from a housing of the surgical device, through the elongated body, and coupled to the integrated circuit. The integrated circuit can receive power and exchanges data over the small gauge wiring. The surgical device can be connected to a processing tower via the single cable. The surgical device can be disposable.

In accordance with example embodiments of the present invention, a system is provided. The system includes a processing tower having an electrosurgical generator and a surgical device. The surgical device includes an elongated body having disposed, at its distal end, a tip that can minimize trauma to surrounding tissue during its advancement, an integrated circuit located within the tip, the integrated circuit having an imaging device, an illumination source, and communication circuitry, and a single cable connecting the integrated circuit to the processing tower. The electrosurgical generator provides power to the imaging device, the illumination source, and the communication circuitry via the single cable.

In accordance with aspects of the present invention, the processing tower can further include a video processor for processing a signal received from the imaging device and a video monitor 156 for displaying the video. The system can further include a wireless transceiver for transmitting signal data from the camera to the processing tower. The surgical device can include a cutting device. The surgical device can be disposable.

In accordance with example embodiments of the present invention, a method for harvesting a blood vessel is provided. The method includes advancing an elongated body having a dissection tip disposed at a distal tip of an elongated body along a main vessel to separate the main vessel and its branch vessels from the surrounding tissue and illuminating the main vessel and its branch with an illumination source within the dissection tip. The method also includes capturing and transmitting image signal, by an imaging device within the dissection tip, to a video processor for displaying an image of the main vessel and its branch vessels to a user, moving, using the image, a first cutting portion and a second cutting portion in a distal direction from a position proximally of the dissection tip to capture a blood vessel between the first and second cutting portions, and capturing, using the image, a blood vessel between the first cutting portion and the second cutting portion.

In accordance with aspects of the present invention, the image signal is transmitted over wiring extending internally through the elongated body to a video processor via a single cable. The single cable can provide power for the cutting portion, the imaging device, and the illumination source from a processing tower. The image signal can be transmitted over wirelessly to a video processor via a wireless transceiver integrated within the distal tip.

BRIEF DESCRIPTION OF THE FIGURES

These and other characteristics of the present disclosure will be more fully understood by reference to the following detailed description in conjunction with the attached drawings, in which.

DETAILED DESCRIPTION

Figure 1:
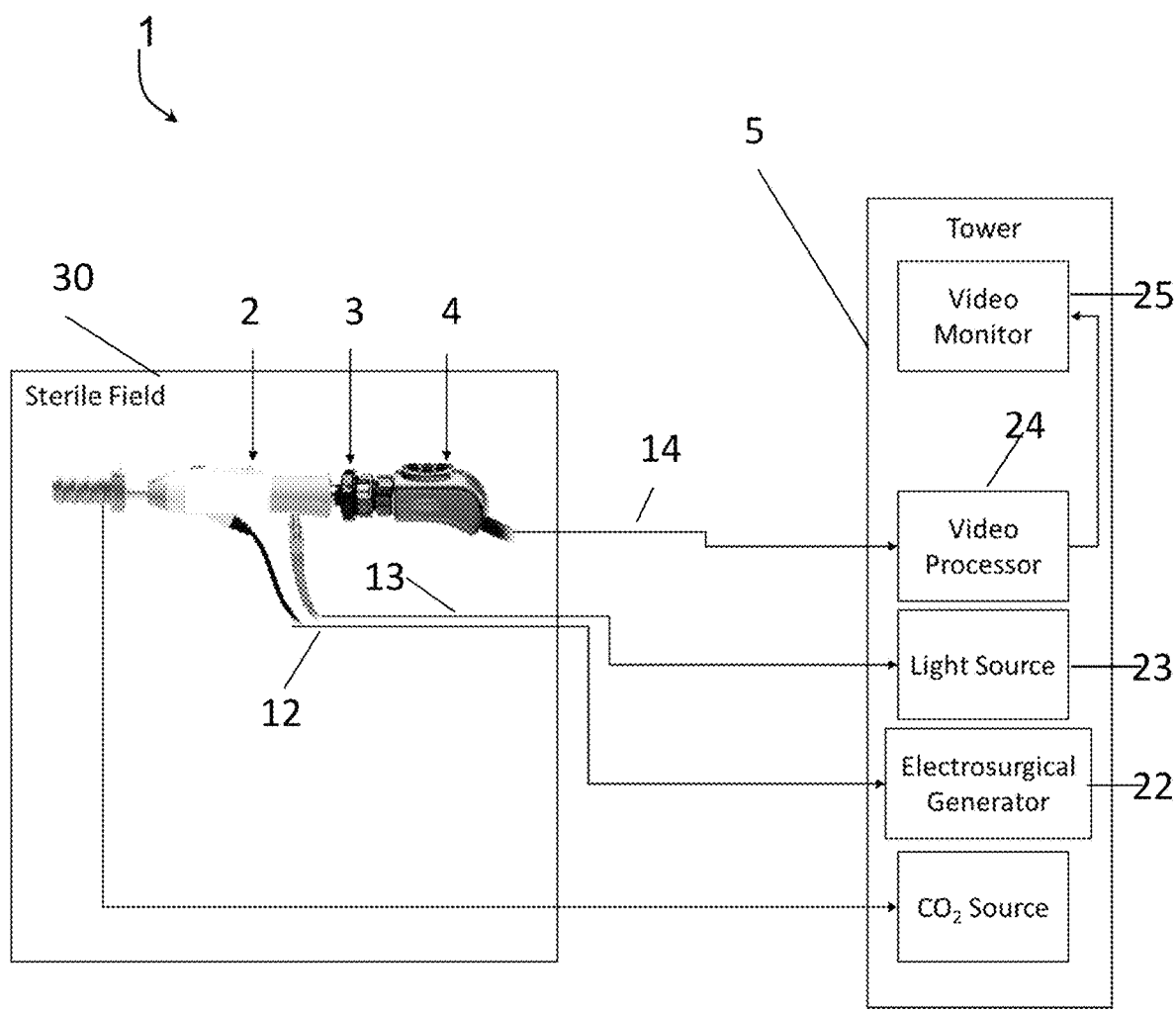
FIG. 1 is an example illustration of a conventional EVH setup including independent components coupled to the EVH device.

The following description provides example embodiments only, and is not intended to limit the scope, applicability, or configuration of the disclosure. Rather, the following description of the example embodiments will provide those skilled in the art with an enabling description for implementing one or more example embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

The present disclosure provides a unitary device for vessel harvesting that reduces an amount of clutter in the sterile field by simplifying the equipment needed to perform the procedure. The present disclosure further replaces previously reusable components with disposable components that do not require re-sterilization. Specifically, the present disclosure incorporates a unique combination of circuitry and wiring to replace the need for modular elements to be combined with a vessel harvesting device for medical procedures. The disposable vessel harvesting device can include an integrated camera and a light source (i.e., light emitting diodes (LEDs)) within a tip of the vessel harvesting device.

The disposable vessel harvesting device can be include or other be compatible with multiple other components for vessel harvesting. For example, the disposable vessel harvesting device can include cutting components as discussed in U.S. Pat. Nos. 9,119,900, 9,498,246, 9,814,481, and 9,943,328 and, all incorporated herein by reference. In such an implementation, the disposable vessel harvesting device can be used to visualize and isolate the main vessel from the surrounding connective tissue by dissecting the main vessel from surrounding connective tissue. The vessel visualization can then introduce a tributary sealing instrument, to seal and sever side branches. Once the side branches are sealed, another device can be used to harvest a section of the main vessel to be used as a bypass graft. The disposable vessel harvesting device of the present disclosure can combine the dissection function, the tributary sealing and severing function, and, optionally, main vessel sealing and severing function, which can result in decreased vessel manipulation and improvement in ease of the procedure. The devices of the present disclosure may also be used to extract the sealed and severed main vessel from the patient.

FIGS. 1 through 6C, wherein like parts are designated by like reference numerals throughout, illustrate an example embodiment or embodiments of improved vessel harvesting device for harvesting vessels, according to the present disclosure. Although the present disclosure will be described with reference to the example embodiment or embodiments illustrated in the figures, it should be understood that many alternative forms can embody the present disclosure. One of skill in the art will additionally appreciate different ways to alter the parameters of the embodiment(s) disclosed, such as the size, shape, or type of elements or materials, in a manner still in keeping with the spirit and scope of the present disclosure.

Referring to FIG. 1, a representative conventional system 1 for performing an endoscopic harvesting procedure is depicted. The system 1 typically includes a reusable endoscopic harvesting device 2 configured to receive a separate reusable endoscope 3 and a reusable camera 4, each separately connected to a central control tower 5. Traditionally, to be reusable, each of the endoscopic harvesting device 2, endoscope 3, and camera 4 must be sterilized and require their own power, data communication lines, and/or processing component extending from the tower 5. As depicted in FIG. 1, for example, the endoscopic harvesting device 2 has a power cable 12 connected to an electrosurgical generator 22, the endoscope 3 has a separate power cable 13 connected to a light source component 23, and the camera 4 has a cable 14 connected to video processor 24 relaying information to a video monitor 25. Additionally, each cable 12, 13, 14 can include their own power sources and power cabling. In operation, each of the components 2, 3, 4 of device 1 would need to be sterilized when being utilized within a sterile field 30 of a procedure.

Figure 2:
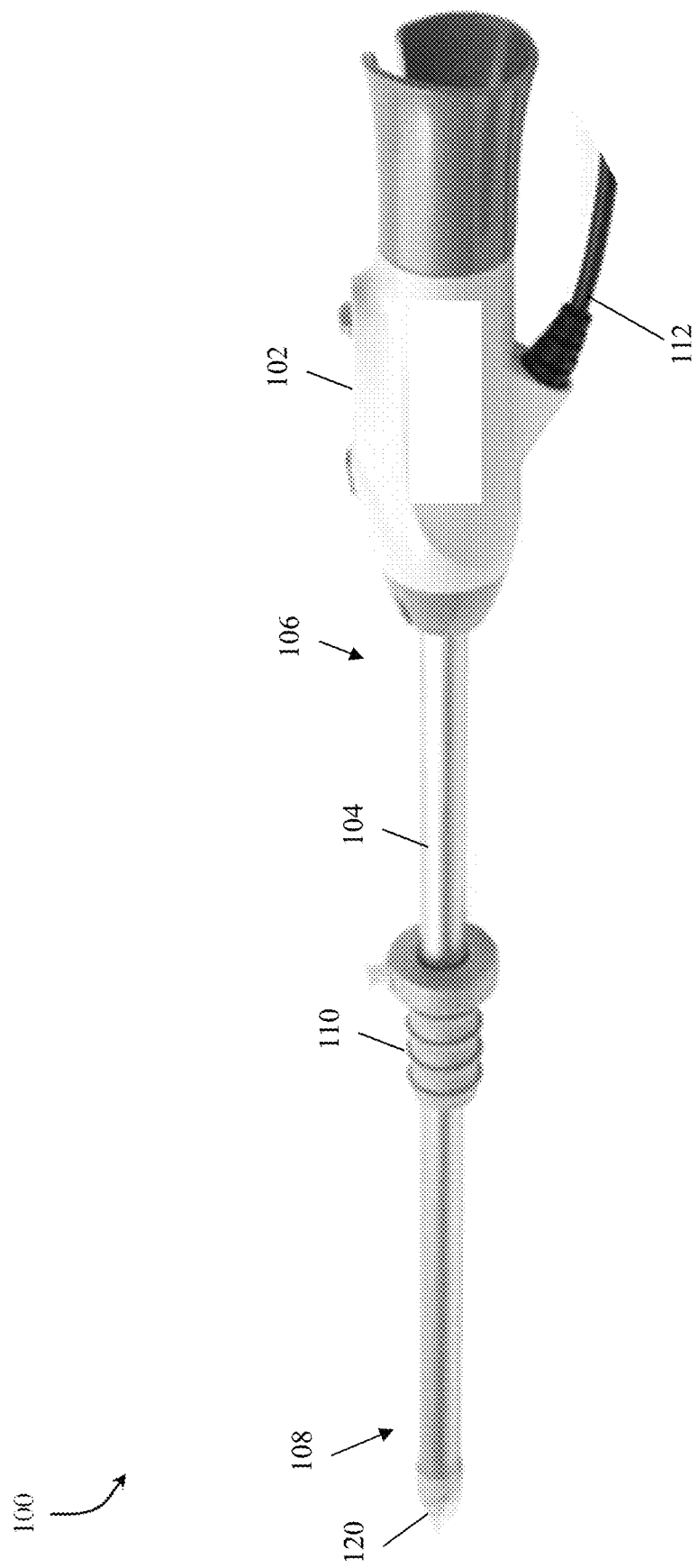
FIG. 2 is an example vessel harvesting device in accordance with the present disclosure.

Referring to FIG. 2, an example vessel harvesting device 100 in accordance with the present disclosure is depicted. The device 100, in some embodiments, includes housing 102 which can be configured to house the various components of the device 100, including internal wiring to receive and deliver power to said components, and communicate data to systems outside of the housing 102. The housing 102 can also include buttons, switches, etc. for controlling operation of the device 100. For example, the housing 102 can include a button for powering a cutting component of the device 100. The housing 102 can be constructed from any combination of materials utilizing any combination of systems and methods known in the art. For example, the housing 102 can be constructed from a biocompatible material, such as, plastic material, elastomeric material, metallic material, shape memory material, composite material or any other materials that has the desired characteristics. In some embodiments, the device 100 and components thereof can be disposable.

In some embodiments, the housing 102 may be coupled to wires or cabling 112 that is configured for providing power and transferring data between the device 100 and the subsystems thereof. For example, the cable 112 can provide power to a combination of an integrated circuit, imaging device, illumination device, transceiver, etc. as discussed in greater detail herein. As would be appreciated by one skilled in the art, the cable 112 can also be configured to provide power to other systems known in the art, for example, a cutting sub-system of the device 100, such as the cutting systems discussed with respect to U.S. Pat. Nos. 9,119,900, 9,498,246, 9,814,481, and 9,943,328 and, all incorporated herein by reference. The cable 112 can provide a combination of wiring for different power and data cabling within a singular shield or can be a combination of wires braided together into a single line. The cable 112 can provide a singular structure that can include any combination of elements that require a physical connection to one or more other devices within the tower 150.

In some embodiments, the cable 112 can include one or more conductive lines for providing power to the housing 102, from an outside source (e.g., control tower 150), for its various functions. The power provided over the one or more conductive lines can be used to power any combination of components that are part of the device 100, for example, a electrocautery lead, a light source, imaging devices, an insufflation device, computing devices, circuit boards, or any combination of devices and electronics that require powering. The cable 112 can include a single conductive line to provide all the power to the housing 102 and the components therein, can include a plurality of separate conductive lines for dedicated power for each of the components within the device, or a combination therefore. The cable 112 can include any combination of conductive lines and light transmission lines for any combination of devices. For example, the cable 112 can include three dedicated lines (e.g., positive, negative, and signal lines) for an electrocautery component, two dedicated lines for an illumination source 208 (e.g., signal line and light transmission line), a dedicated line for an imaging device 204 (e.g., signal line) all positioned within the device 100. In some embodiments, the one or more conductive lines are wires including any combination of wire gauge. The cable 112 can also include different gauge wires to provide different levels of power to different components of the device 100.

In some embodiments, the cable 112 can include one or more optical fibers that are designed to carry light. The one or more optical fibers can be used to transmit light from a light source outside of the device 100 (e.g., from the tower 150) to an illumination source within the device 100 (e.g., illumination source 208). In some embodiments, a combination of the one or more conductive lines and the one or more optical fibers (e.g., fiber optics) can be used to transmit data and/or signals to and from a computing device (e.g., video processor 154) located remotely from the device 100 (e.g., from the tower 150) to a device within the device 100 (e.g., integrated circuit 200). For example, the one or more conductive lines and/or the one or more optical fibers can be used to transmit signal wires from a imaging device 204 within the device 100 to a video processor 154 separate from the device 100.

In some embodiments, the cable 112 can include additional functional elements. For example, the cable 112 can include channels for providing $CO_2$ for insufflation, fluids, saline for washing/irrigation, etc. The cable 112 can be coupled to any portion of the device 100 using any combination of coupling mechanisms. For example, it can be a removeable cable 112 inserted into a port on the device 100 or it can be a fixedly attached cable 112 coupled to contacts within the device 100.

In some embodiments, an elongated body 104 can extend from the distal end of the housing 102. The elongated body 104 can be substantially solid or hollow and have a proximal end 106 and a distal end 108. The proximal end 106 can be coupled to and/or within the housing 102 using any combination of coupling mechanisms. In some embodiments, the elongated body 103 can include an inner cavity extending from the proximal end 106 to the distal end 108 to enable power and/or data transmission lines to extend between the proximal end 106 and the distal end 108 to the housing 102 and the cable 112 coupled to the housing 102. As would be appreciated by one skilled in the art, the elongated body 104 can house and/or be coupled to a variety of other tools or components, for example, a cutting tool. In some embodiments, components can be inserted on/around the device 100. For example, a trocar 110 can be removably slide onto the elongated body 104 of the device 100.

In some embodiments, the elongated body 104 can be configured for passing extravascularly through an entry incision to a vessel harvesting site. To aid in navigating the elongated body 104 to a site of harvesting, the elongated body 104 may be sufficiently rigid axially along its length. To provide the elongated body 104 with such characteristic, in an embodiment, the elongated body 104 may be made from a biocompatible material, such as, plastic material, elastomeric material, metallic material, shape memory material, composite material or any other materials that has the desired characteristics. To the extent desired, the elongated body 104 may be provided with some flexibility to move radially or laterally from side to side depending on the application.

In some embodiments, the elongated body 104 of the device 100 may be solid. In other embodiments, the device 100 may include one or more lumen with lumen that accommodate advancing instruments, wires, power/data lines, or materials therethrough. In some embodiments, the device 100 may include a conduit through which wires or cabling may be advanced for powering and/or communicating with electrical components within the device 100.

Figure 3A:
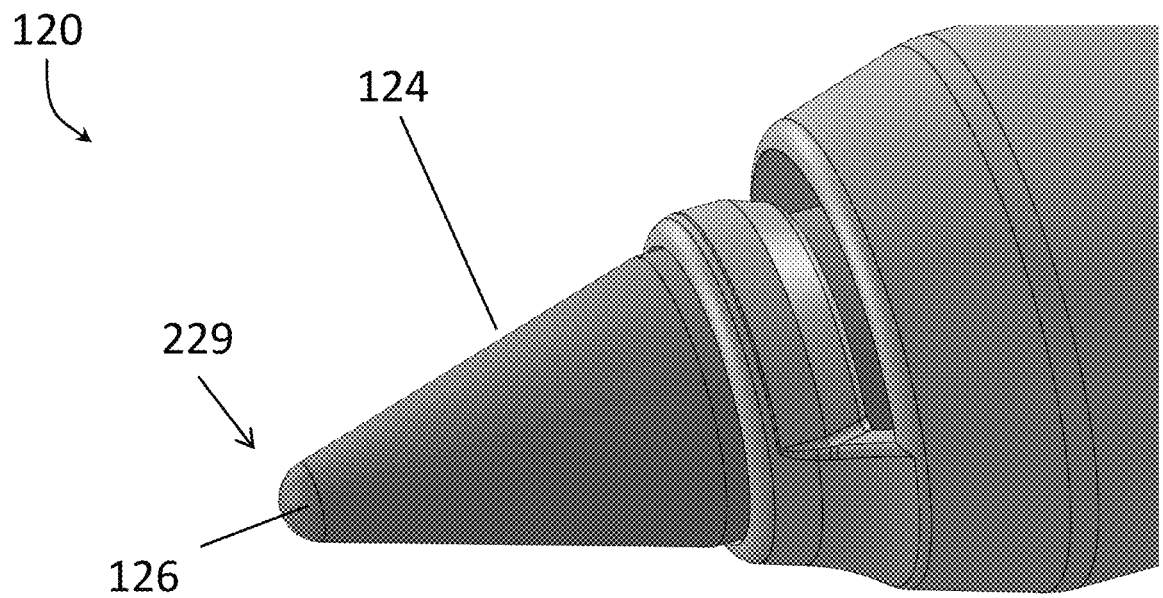
FIGS. 3A and 3B are example dissection tips for a vessel harvesting device in accordance with the present disclosure.
Figure 3B:
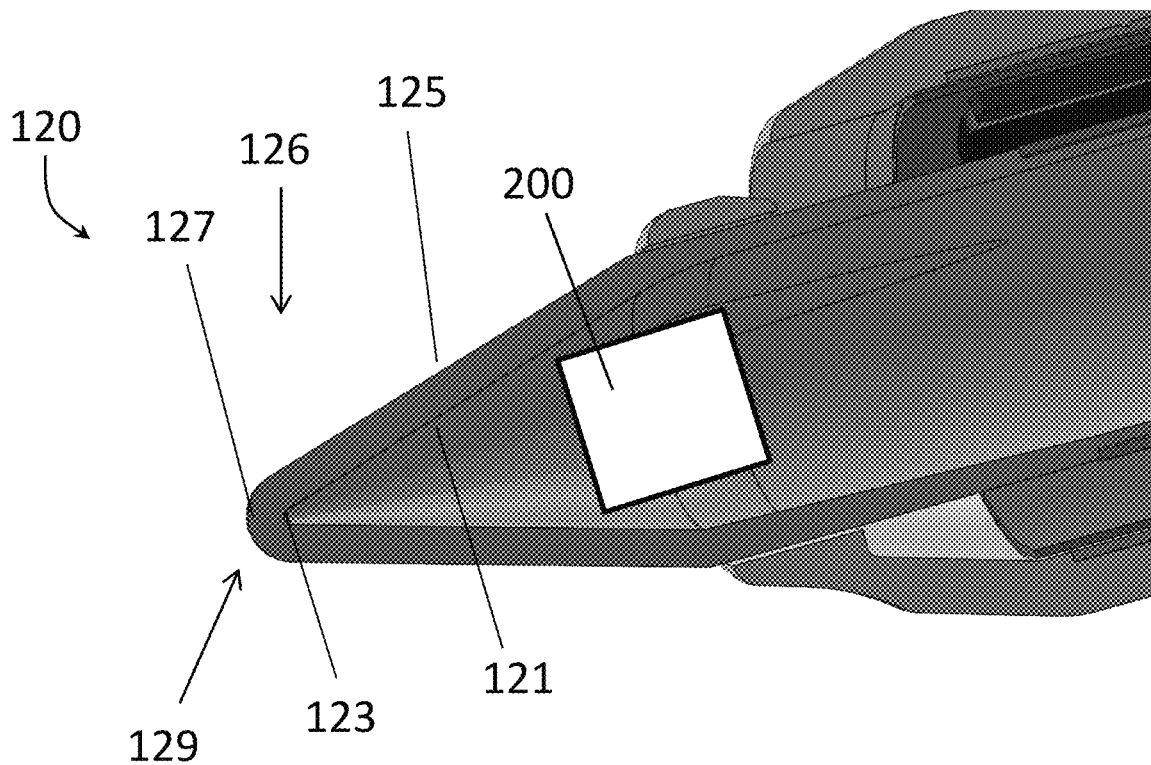

In some embodiments, the elongated body 104 can terminate at a dissection tip 120 or can have a dissection tip 120 coupled to the distal end 108 of the elongated body 104. Referring to FIGS. 3A and 3B, example depictions of a dissection tip 120 are provided. FIG. 3A depicts an isometric view of an example dissection tip 120. In some embodiments, the dissection tip 120 may include a generally tapered section 124 which terminates in a generally blunt end 126 for atraumatic separation of a vessel segment, being harvested from surrounding tissue, while minimizing or preventing tearing or puncturing of nearby vessels or tissue as the device 100 is navigated along a vessel segment. Although illustrated as being blunt, it should of course be understood that, to the extent desired, the end 126 of the dissection tip 120 may be made relatively pointed to enhance advancement of the distal end of the device 100. Similarly, the tapered section 124 may be configured differently structurally to enhance the operability of the device 100.

In some embodiments, to reduce likelihood of trauma during a dissection process, in some embodiments, the dissection tip 120 may be radially pliable, flexible or deformable so that the dissection tip may deflect slightly under exertion of force applied to the dissection tip 120. In some embodiments, the dissection tip 120 is radially compressible so that the walls of the dissection tip 120 can deform under exertion of force normal to the tip surface. To that end, the dissection tip 120 may be formed from thin wall plastic material to enable the dissection tip to flex under load. Suitable materials include, but are not limited to, polycarbonate, polyethylene terephthalate glycol-modified (PETG), polyethylene terephthalate (PET) and other materials that provide enough optical clarity while allowing the dissection tip to flex under load. At the same time, the dissection tip 120 may be provided with sufficient column strength in axial or longitudinal direction to allow dissection of the vessel from the surrounding connective tissue. In other words, while being axially rigid to permit advancement of the tip 120 through tissue, tip 120 may be radially pliable, flexible or deformable. Other characteristics of the dissection tip 120 are contemplated, such as having variable strengths: (1) in an axial direction versus a longitudinal direction, wherein the axial strength is greater than the longitudinal strength; (2) in a longitudinal direction versus an axial direction, wherein the longitudinal strength is greater than the axial strength; or (3) the axial direction versus a longitudinal direction, wherein the axial strength is approximate the longitudinal strength. It is also possible that the dissection tip 120 may include two or more materials, wherein at least one material can have different material properties, such as elasticity, hardness, tensile strength.

Continuing with FIG. 3A and FIG. 3B, in some embodiments, the dissection tip 120 may be cone shaped, and may be shaped at its distal end 129 in a manner so as to minimize the negative effects of visual distortion or blinding at the center of the field of visualization when viewing through an imaging device (e.g., a camera) within the dissection tip 120. Internal surface 121 of the dissection tip 120 may be tapered, with a relatively constant slope toward the distal end 126 of the dissection tip 120, terminating at an internal apex 123, which may be a sharp point, as shown in FIG. 3B. External surface 125 of the dissection tip 120 may also be tapered with a constant slope toward the distal end 126 of the dissection tip 120; however, at the distal end 126, a relatively rounded, blunt end may be formed to minimize tissue damage during dissection. As illustrated, at the distal end 106, the external surface 125 of the dissection tip 120 may be folded back on itself in a proximal direction to then terminate at an external apex 127, maintaining the blunt exterior surface and forming an indent in the distal end of the dissection tip 120.

In some embodiment, both the internal apex 123 and the external apex 127 may be collinear with the central longitudinal axis of the cannula 100. In other words, the centers of the internal apex 123 and the external apex 127 can be located on the central longitudinal axis of the elongated body 104. By providing an apex on each of the internal surface 121 and the external surface 125 of the dissection tip 120 that are also collinear with the axis any imaging device within the dissection tip 120, those surfaces perpendicular to the light path (which is parallel to the axis of the elongated body 104) may be eliminated, which then may eliminate light refraction from the perpendicular surface back into the camera and, thus, may minimize or eliminate the visual distortion or blinding when viewing through an internal imaging device with a light source and camera system.

Referring to FIG. 3B, in some embodiments, the dissection tip 120 may include an inner cavity in fluid communication with an inner cavity of the elongated body 104 to enable power and data communication to be delivered between the dissection tip 120 and the housing 102. This can also include sending and receiving power and data to/from the dissection tip 120 to the cable 112 and to the tower 150.

FIG. 3B depicts a cross-sectional view of an example dissection 120 with an inner cavity. In some embodiments, a specialized integrated circuit 200 configured for illumination and/or electronic imaging may be integrated within the inner cavity of the dissection tip 120 for capturing image data outside of the dissection tip 120. The specialized circuit 200 can be sized and dimensioned to fit within the dissection tip 120 of the device 100 and positioned at a location in which imaging can be captured from within the dissection tip 120. For example, the dissection tip 120 can have a circular cross section of approximately 2-10 mm in diameter and positioned at the distal end of the dissection tip 120.

Figure 4:
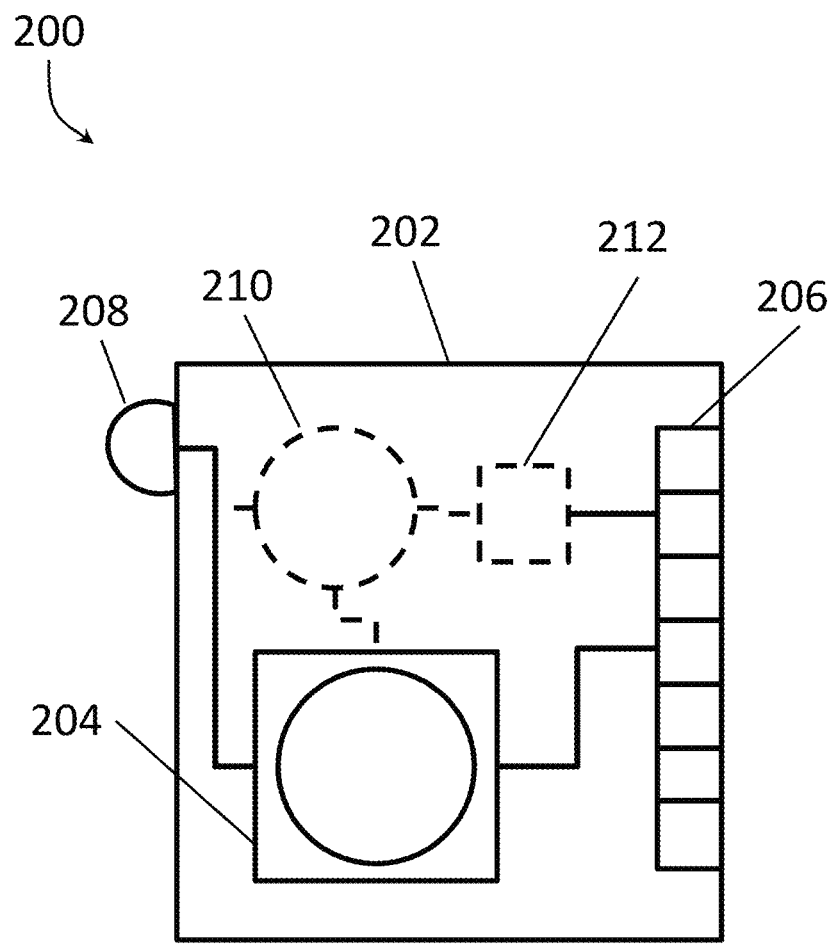
FIG. 4 is an example specialized integrated circuit for a dissection tip of a vessel harvesting device in accordance with the present disclosure.

Referring to FIG. 4, an illustrative diagram of an example specialized circuit 200 for use within the dissection tip 120 is depicted. In some embodiments, the specialized circuit 200 can include a customized printed circuit board 202 with any combination of an imaging device 204, communication circuitry 206, illumination source 208, a battery 210, a wireless transceiver 212 mounted thereon. The imaging device 204, communication circuitry 206, illumination source 208, the battery 210, and the wireless transceiver 212 can be embedded within or on the printed circuit board 202 in any combination of methods known in the art.

In some embodiments, the imaging device 204 can include any combination of digital imaging devices that are sized and dimensioned to fit on a circuit board 202 and positioned within the dissection tip 120. For example, the imaging device 204 can be a camera designed to take any combination of images and videos. The size and resolution of the imaging device 204 can be influence the size of the specialized circuit 200. For example, the higher the resolution, the larger the imaging device 204 may be increasing the required size of the specialized circuit 200. In some embodiments, the imaging device 204 can be designed to capture light, convert the captured light into a signal, and transmit the signal along the cable 112 to a destination device (e.g., tower 150). In some embodiments, the imaging device 204 can include a lens and camera chip mounted on circuit board 202 at the tip of the device 100. The ambient light can pass through the glass lens and the early camera processing can be processed (e.g., on the circuit board 202) within the tip 120 of the device 100. This process can be performed without having to sending ambient light all the way down fiberoptic rods or other methods within the handle for processing. The pre-processed electrical signal can be sent from the circuit board 202 sent along transmission lines over the cable 112 to the video processor 154 that is either embedded in the handle 102 or in an external tower 150.

In some embodiments, the communication circuitry 206 can include any combination of electrical contacts, transceivers, plugs, wiring, etc. configured to transmit data to and from the imaging device 204 over wiring to cable 112 for transmission of power and/or data to and from the device 100 to remote source (e.g., tower 150). For example, the communication circuitry 206 can be any combination of a hard-wired bus, channel, pins, etc. for communicating data over transmission lines, such as small gauge wires (or any wiring/conductive elements known in the art), extending through the elongated body 104 to the housing 102. In some embodiments, the communication circuitry 206 can be different types of transmissions lines than the transmissions lines found within the cable 112.

In some embodiments, the printed circuit board 202 can include or otherwise be attached to an illumination source 208, for example, light emitting diode(s) (LED) configured to illuminate the surrounding area near the tip 120 for image capture by the imaging device 204. The illumination source 208 can include any combination of light sources, such as LEDs, known in the art and can be configured to provide illumination within a vessel. With all the components on the specialized circuit 200 located internally within the dissection tip 120, the device 100 may not require a separate endoscope, light source, camera and each of their associated external cablings, as discussed in greater detail with respect to FIGS. 5A and 5B.

In some embodiments, the device 100 can be sterile out of its packaging without the need to attached separate components that need sterilization (e.g., endoscope, camera, light, etc.) and the entire device 100 can be disposed of after use. In conventional medical devices 1, that are used as part of medical procedure, can include a separate reusable camera 4 that use traditional rigid rod lenses which pass captured images from a separate reusable endoscope 3 to a camera 4. A rigid rod lens can be part of a separate device, such as an endoscope 3, with a glass lens at the tip. The ambient light that enters the lens is focused and travels up fiber optic rods in the rod shaft back to an eyepiece. The camera 4 is attached to the eyepiece and takes that light and processes it and then sends that signal over it's own wiring to a video process 24 and then out to a monitor 25.

Such devices 1 can also pass light from an endoscope 3, which can be very expensive, necessitating that they are used as reusable devices 1. Reusable devices need to then be sterilized before reuse, with each of the separate components being individually sterilized (e.g., endoscope, camera, light, etc.). In particular, such traditional devices 1, use separate external cameras 4 that require the use of an expensive light source box 23 within a tower 5. The light source box 23 can generate light to be passed along a separate cable 13 and through the rod lens out the tip and into the body of the vessel harvest device 2. During the procedure, light inside the body passes back through the rod lens to an expensive camera 4 attached to the rod lens proximally which processes the light and makes the image, sending that back to a similarly expensive video processor 24.

In contrast, in accordance with the present disclosure, there is no need for a separate light source box in the control tower 150 because the specialized circuit 200 has an imaging device 204 and one or more illumination sources 208 (e.g., LEDs) thereon. This combination of elements is significantly cheaper because they only need two simple wiring to deliver power to the illumination sources 208 to create light distally within a body. Additionally, the combination of the illumination sources 208 and the imaging device 204 do not require expensive components like a rod lens that necessitates transferring light generated in light boxes and transmit it to the location since light is generated by the illumination sources 208 within the dissection tip 120. Similarly, the device 100 of the present disclosure does not require an expensive rod lens to deliver the image back to a camera because the imaging device 204 is placed distally on the specialized circuit board 200 within the dissection tip 120. Having cost effective components, such as the imaging device 204 and the illumination sources 208 within a specialized circuit board 200 that are coupled to cost effecting power and data lines within the cable 112 provides a compact device 100 for disposable one-time use.

In some embodiments, the dissection tip 120 may be transparent to allow for illumination through (e.g., via illumination source 204) and viewing through the tip 120 (e.g., via the imaging device 204), for example, while procedures are performed using the device 100. The dissection tip 120 in some embodiments, may be provided with any shape as long as it facilitates image capturing (e.g., by imaging device 204) therethrough, and allows for necessary control during tissue dissecting, i.e., separation. Similarly, the positioning of the specialized circuit 200 within the dissection tip 120 can be located and oriented in a manner that facilitates sufficient illumination and image capturing therethrough, and allows for necessary control during tissue dissecting.

In some embodiments, the combination of the shape and material of the dissection tip 120 in combination with the positioning of the imaging device 204 and the illumination source 208 can facilitate sufficient light to enable a capturing image data of sufficient quality for use during a procedure. The illumination source 208 can have one light source at a single location or multiple light sources at multiple locations to provide the preferred lighting for image capture by the imaging device 204. For example, the illumination source 208 can include multiple light sources (e.g., 4-12 LEDs) laid out in a distributed and symmetrical pattern to ensure even light distribution (e.g., circular ring pattern). In some embodiments, when there are multiple light sources within illumination source 208, the can be wired to be controlled as a single unit or controlled individually. Similarly, specialized circuit 200 the imaging devices 204 and/or different types of imaging devices 204.

Continuing with FIG. 4, in some embodiments, the specialized circuit 200, and components thereon, can receive power over and transmit data over the single cable 112 coupled to the housing 102 to a processing unit(s) (e.g., video processor 154) within a control or processing tower 150. In some embodiments, the cable 112 can be directly or indirectly connected to the communication circuitry 206 to provide data communication and power to the circuit 200. For example, the cable 112 can include one or more conductive and/or optic lines for transmitting signals, such as image data, from the imaging device 204 to the tower 150 for video processing and display. Power and data can be conveyed from the cable 112 attached to the housing 102, through the elongated body 104, and to the specialized circuit 200. For example, small gauge wires coupled to the cable 112 within the housing 102 and extending through the elongated body 104 between the dissection tip 120 and the housing 102 can be used to deliver power to the illumination source(s) 208 and transmit control and video signals between the imaging device 204 to an external video processor 154.

In some embodiments, the specialized circuit 200 and/or the housing 102 can optionally include a battery 210 for powering the imaging device 204, illumination source 208, and/or other components within the device 100. The battery 210 can be designed to provide the power for the specialized circuit 200 and the electrical components/devices thereon (e.g., imaging device 204, illumination devices 208, etc.). The battery 210 can be used to supplement or replace the power being supplied from the tower 150. In some embodiments, the battery 210 can be rechargeable such that power supplied through the cable 112 or another cable can provide energy to charge the battery 210 within the housing 102 of the device 100. The battery 210 may be able to hold a charge to sufficiently power the device 100 and all of the components thereon for the duration of a medical procedure.

Figure 5A:
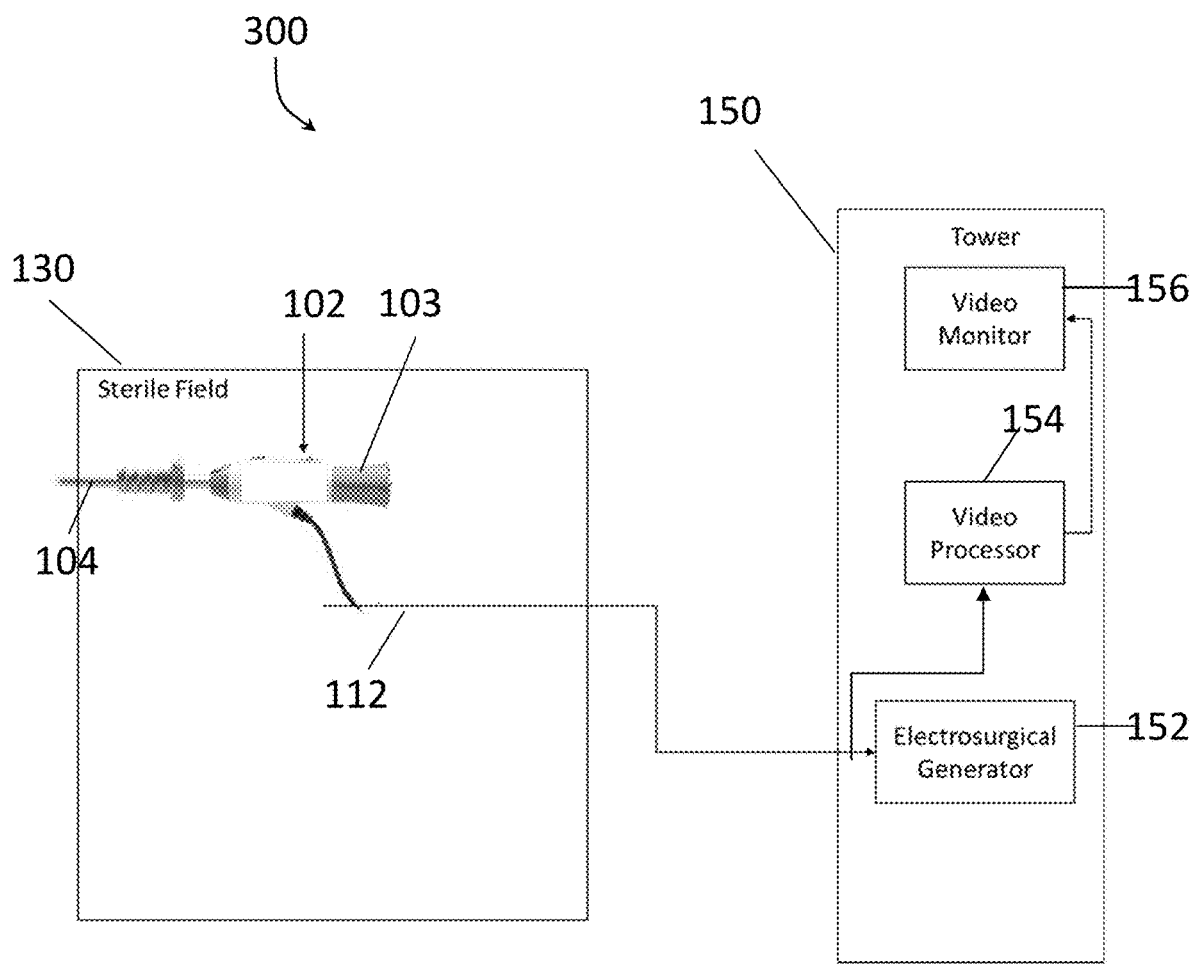
FIGS. 5A and 5B are example systems for use with a vessel harvesting device in accordance with the present disclosure.

Referring to FIG. 5A, an example system 300 with the specialized circuit 200 wired for power and data transmission to a location external to the device 100 is depicted. In some embodiments, the system 300 can include the device 100, as discussed with respect to FIG. 2, coupled to a processing tower 150 via the cable 112. The cable 112 can be configured to receive power from a power supply within the tower 150 and share data with one or more processing units within the two 150. The tower 150 can include a combination of processing units responsible for managing the various sub-systems of the device 100. In some embodiments, the processing units can include an electrosurgical generator 152, a video processor 154, and a video monitor 156. The electrosurgical generator 152 can be configured to provide and control the power to the device 100 for performing electrosurgical tasks, for example, imaging, illumination, cauterizing, cutting, etc. The video processor 154 can be configured to receive (e.g., via cable 112), interpret, transform, and relay video signal data provided by the imaging device 204 within the device 100. The video processor 154 can also convey video signals in a displayable format to the video monitor 156 for displaying to a user. In some embodiments, the electrosurgical generator 152, the video processor 154, and the video monitor 156 can all be integrated within a single compact device.

In some embodiments, the cable 112 can include separate wires for transmitting the video signal from the wires providing electrosurgical power to the device 100. For example, at or within the tower 150, the cable 112 can be split into two separate wirings for separate connections into the electrosurgical generator 152 and the video processor 154. In other words, the combination of wires integrated into the single cable 112 can bifurcate at the tower 150 to connect to each respective processing unit, such that the experience of the user is unchanged because only one cable 112 leaves the device 100 in the sterile field 130, unlike the multiple cables required to operate the system 1 of FIG. 1. In some embodiments, the video processor 154 can also provide power to the specialized circuit 200 and illumination source 208 through the separate video signal wires integrated into the single cable 112. This configuration can be used in addition to or in place of the electrosurgical generator. Additionally, with the integrated imaging device 204 on the specialized circuit 200, there is no need for a separate the rigid endoscope with its own cabling and separate light source with its own cabling.

Figure 5B:
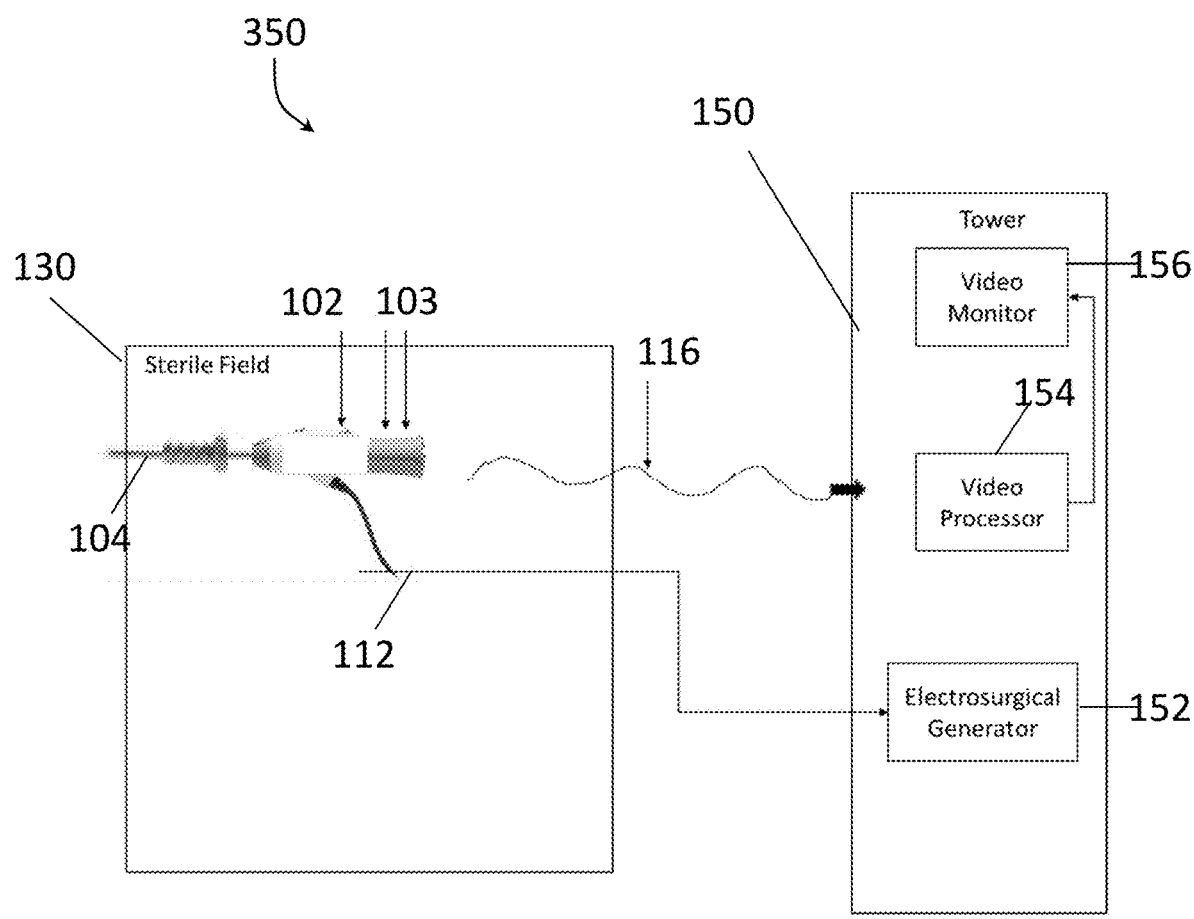

Referring to FIG. 5B, an example system 350 in which the specialized circuit 200 is configured for wireless power and data transmission is depicted. In some embodiments, the system 350 can include the device 100, as discussed with respect to FIG. 2, coupled to a processing tower 150 via the cable 112. The cable 112 can be configured to receive power from an electrosurgical generator within the tower 150. The tower 150 can include a combination of processing units responsible for managing the various sub-systems of the device 100. In some embodiments, the processing units can include an electrosurgical generator 152, a video processor 154, and a video monitor 156. The electrosurgical generator 152 can be configured to provide and control the power to the device 100 for performing electrosurgical tasks, for example, cauterizing, cutting, etc. The video processor 154 can be configured to receive (e.g., via transceiver 116), interpret, transform, and relay video signal data provided by the imaging device 204 within the device 100. The video processor 154 can also convey video signals in a displayable format to the video monitor 156 for displaying to a user.

Continuing with FIG. 5B, in some embodiments, the specialized circuit 200 and/or the housing 102 can also include a wireless transceiver 212, included within or others coupled to the communication circuitry 106, for communicating data to and from external processor(s) (e.g., video processor 154). The data from the imaging device 204 can be transmitted back to the tower 150 using any combination of methods for processing and/or viewing. The signal can be transmitted either wirelessly from the wireless transceiver 212 and/or data lines within cable 112 back to a video processor 154 in the tower 150 and then out to the video monitor 156. In some embodiments, the wireless transceiver 212 can be powered by the battery 210 and/or through the cable 112 and can be configured to transmit data in any wireless format known in the art, for example, Bluetooth, Wi-Fi, RF, etc. In some embodiments, the combination of an onboard battery 210 and transceiver 212, the dissection tip 120 can operate independently from the rest of the device 100, without the addition of wiring in the elongated body 104 of cable 212. As would be appreciated by one skilled in the art, any combination of the illumination source(s) 208, battery 210, and transceiver 212 can be located on the specialized chip 200 or communicatively attached to the specialized chip 200 from a separate location. For example, the battery 210 and/or transceiver 212 can be located on a circuit board within the housing 102 and coupled to the specialized chip 200 through wires extending through the elongated body 104 of the device 100. In this example, any video signals from the imaging device 204 would be transmitted from the specialized chip 200 to the circuit board within the housing 102 via the internal wiring.

In some embodiments, the onboard illumination devices 208 for illumination, imaging device 204, and power for the specialized circuit 200 can be provided via the battery 210 and the image data (and other data signals) can be transmitted via a wireless transceiver 212. The video processor 154 can be configured with a corresponding transceiver for communicating with the transceiver 212 on the device 100. In some embodiments, the communication medium, frequency, etc. of the wireless data transmission can be adjusted to avoid interference with other devices in the area.

Providing independent power and lighting for the specialized circuit 200 with the optional combination of the wireless transmission of video signals enables an unchanged user experience because only one cable 112 leaves the device 100 in the sterile field 130, unlike the multiple cables required to operate the system 1 of FIG. 1. In some embodiments, a power supply can be coupled to the device 100, without the need of the cable 112 (e.g., a battery 210), to power the other components. For example, the device 100 can be adapted for use without the cable 112 by having a battery 210 with sufficient power to power the illumination devices 208, imaging device 204, and communication means (transceiver 212 or communication path 206) for exploratory procedures. In another example, the device 100 can utilized additional power from the cable 212 to power more power intensive components, such as an electrosurgical cutting tool. Additionally, with the integrated imaging device 204 on the specialized circuit 200, there is no need for a separate the rigid endoscope with its own cabling and separate light source. The battery 210 would power the illumination devices 20 at the end of the device 100 and the transmitter to deliver the video signal to the video processor 154 within the tower 150. The combination of features of the present disclosure provides a simple system which can be adapted for different procedures.

Figure 6A:
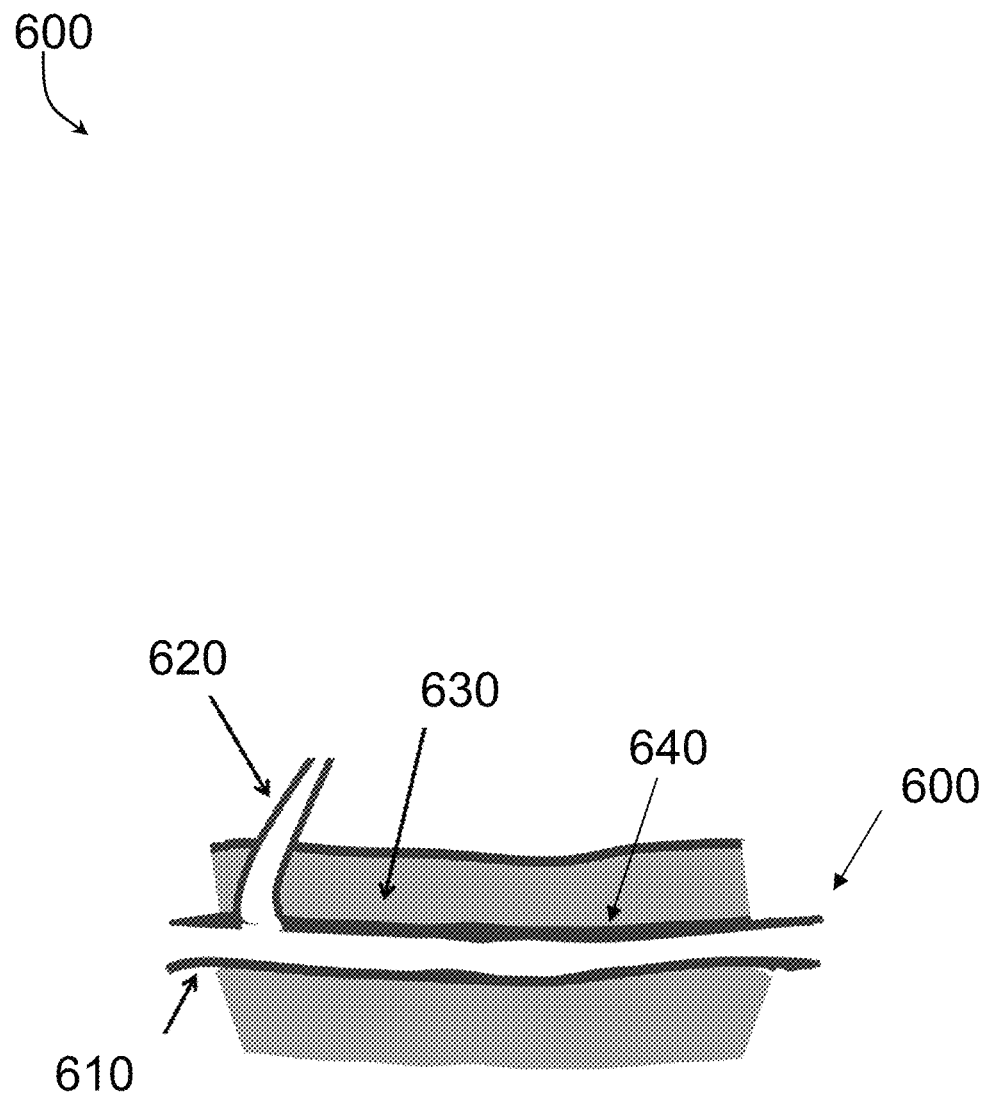
FIGS. 6A, 6B, and 6C are example procedures provided using an vessel harvesting device in accordance with the present disclosure.
Figure 6B:
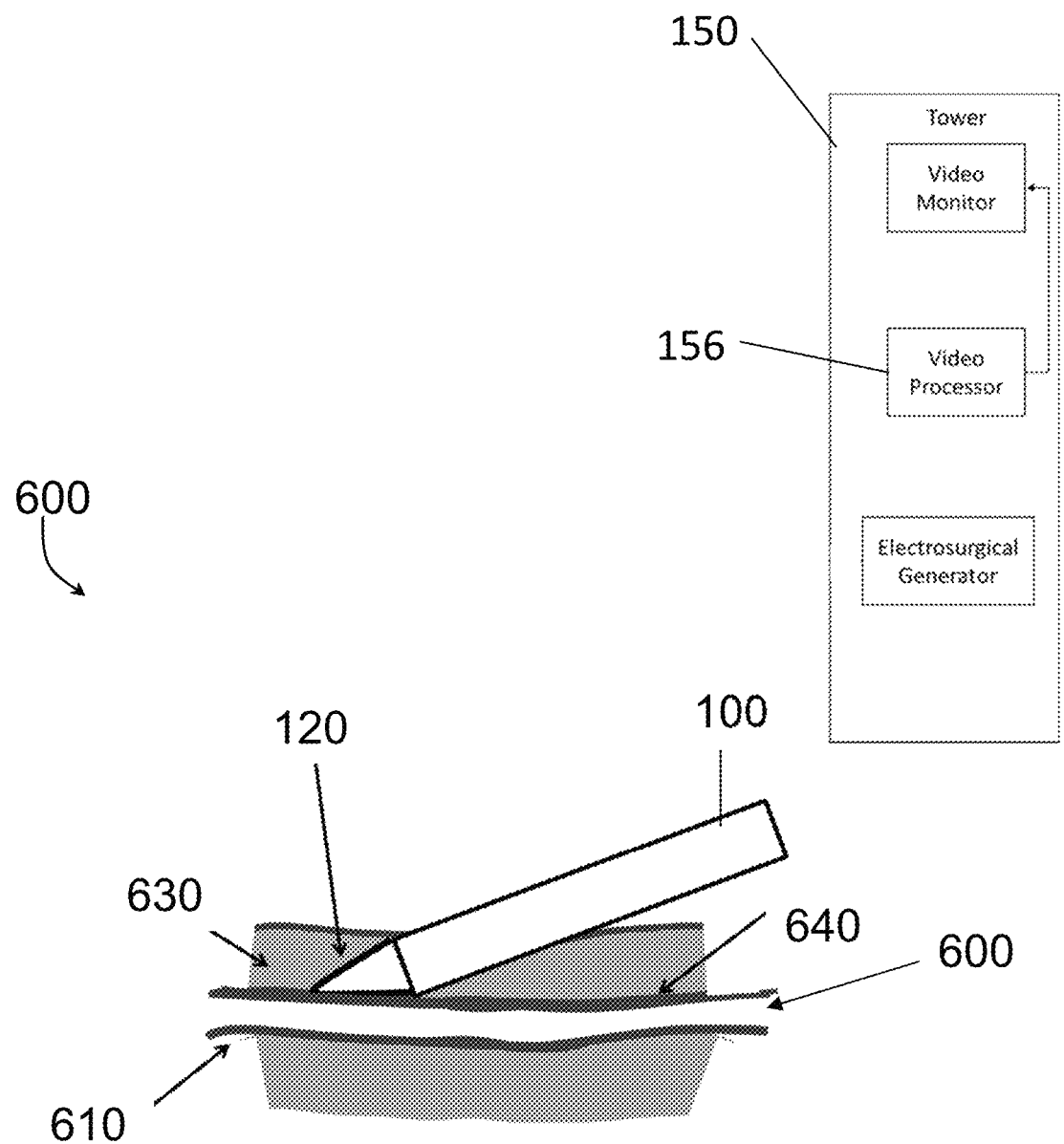
Figure 6C:
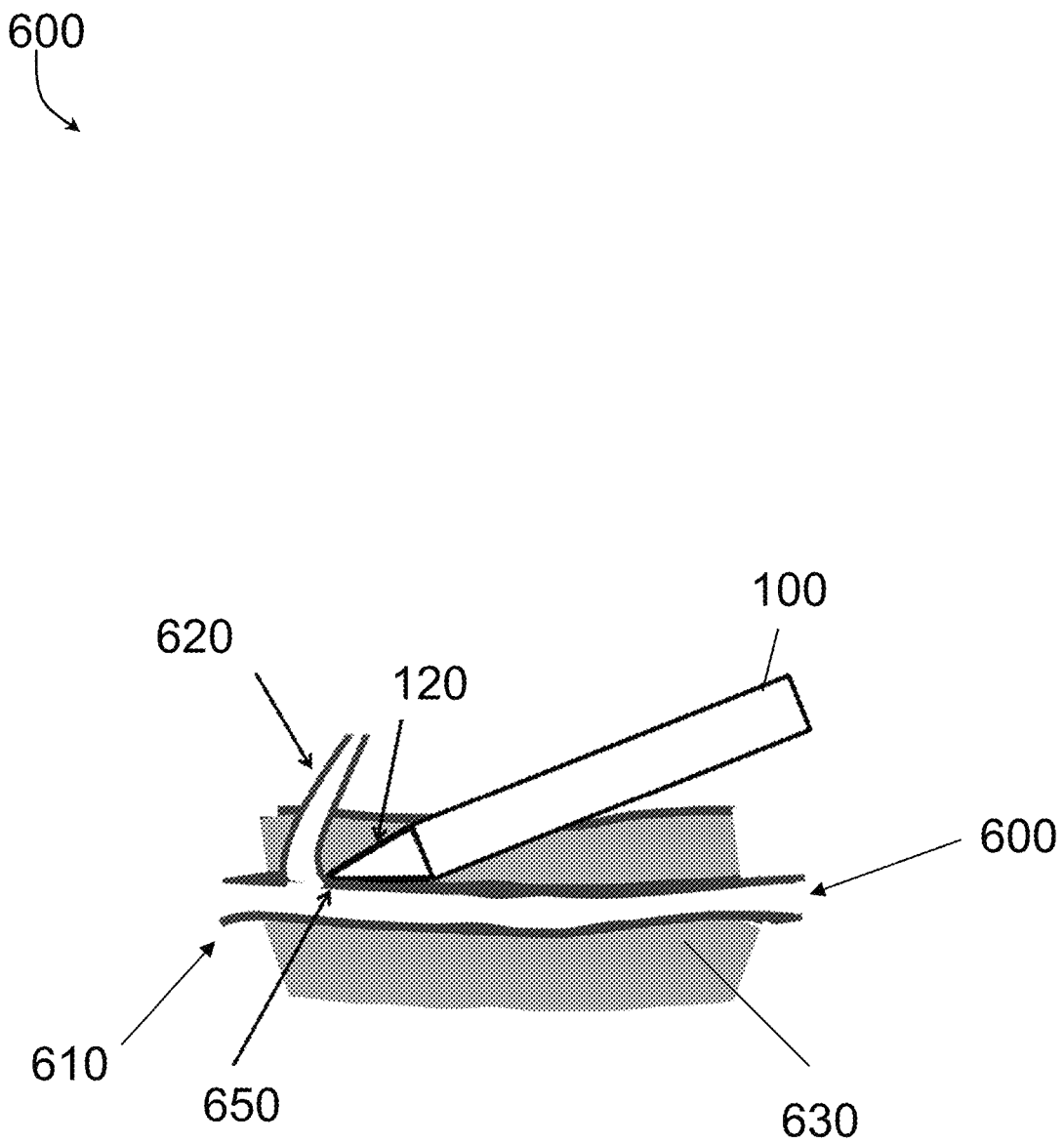

In reference to FIGS. 6A-6C, a vessel 600 can be composed of a main trunk 610 and branch vessels 620 that emanate from the vessel trunk 610, as shown in FIG. 6A. The vessel 600 and its branches 610 are encased in subcutaneous fatty connective tissue 630, and need to be dissected free of the surrounding fatty connective tissue 630 before the main vessel 600 may be harvested. The subcutaneous fat 630 is softer than skin, muscle, fascia or other connective tissues. Although adherent to the vessel 600, the fatty connective tissue 630 forms an interface 640 with the vessel 600 that may be cleanly dissected; that is, there is a natural dissection plane between the outer layer of the vessel 600 (the adventitia), and the surrounding subcutaneous fat 630.

FIG. 6B illustrates an example dissection of the main trunk 610 of the vessel 600 along the natural dissection plane, with the dissection tip 120 of the device 100 being advanced along the adventitial surface of the vessel 600. Isolation of the vessel 600 from surrounding fatty connective tissue 630 along this plane, typically, does not require high dissection forces. The advancement of the dissection tip 120 can be performed with the assistance of the imaging device 204 and illumination source 208 within the dissection tip 120. For example, the illumination source 208 can provide sufficient lighting for the imaging device 204 to capture image data. The image data can then be transmitted through the elongate body 104 to the housing 102. For example, the image data can be transmitted by the imaging device 204 to the communication circuitry 206 then through internal wiring through the elongate body 104. Thereafter, the image data can be transmitted from the housing 102 through the cable 112 into the tower 150 for processing. Optionally, the image data can be transmitted to a wireless transceiver 212 to the tower 150. Within the tower 150, the image data can be processed by the video processor 154 for display on the video monitor 156 for viewing by user performing or assisting in the procedure. In some embodiments, the dissection tip 120 may be provided with sufficient column strength to dissect the vessel 600 from the surrounding tissue 630 along the natural dissection plane between them.

As illustrated in FIG. 6C, when the dissection tip 120 approaches a branch vessel 620, the dissection tip 120 may catch the branch vessel 620 at a junction 650 between the branch vessel 620 and the main vessel 600. Application of excessive force with the dissection tip 120 may avulse the branch vessel 620 and sever it from the trunk vessel 610, or may otherwise cause damage to the main vessel 600. To that end, in some embodiments, the dissection tip 120 is provided with sufficient column strength to dissect the vessel 600 from the surrounding tissue 630 along the natural dissection plane between them, while being sufficiently pliable to deform or deflect from the branch vessel 620 with the application of increased force, to decrease the potential of trauma to the graft vessel during dissection around branch vessels. It should of course be understood that the rigidity of the dissection tip 120 may be varied from fully flexible to semi-rigid to rigid, in accordance with requirements of the procedure.

In some embodiments, the imaging device 204 and illumination source 208, as discussed with respect to FIGS. 4-5B, may be used to assist a user in the dissection process by conveying a viewable image proximate to the dissection tip 120, as discussed in greater detail herein. In some embodiments, the device 100 may further include one or more end-effectors for cauterizing or sealing and cutting a blood vessel, either a branch vessel or the main vessel. The one or more end-effectors can be powered view the cable 112. For example, the cable 112 can be coupled to an electrosurgical generator 152 that provides power via one or more conductive lines within the cable 112 to the housing 102. At the housing 102, the cable 112 can transfer the power to one or more lines within the housing 102 and through the elongate body 104 to be provided to the one or more end-effectors. In some embodiments, the cable 112 can also carry signals to the one or more end-effectors for activating and deactivating the power or the activation or deactivation can be performed locally on the housing 102 of the device (e.g., via a button on the housing 102).

In operation, the device 100, configured with tip 120 within system 300 or 350, can be utilized to perform various electrosurgical procedures, for example, harvesting blood vessels. Blood vessels can be used in bypass grafting (e.g. greater saphenous vein or radial artery) and can be harvested from the subcutaneous space, beneath the surface of the skin. In some embodiments, an example process for harvesting a blood vessel can be performed using the device 100 discussed with respect to FIGS. 2-6C. The process can include advancing the elongated body 104 with the dissection tip 120 disposed at a distal end 108 of the elongated body 104 along a main vessel 600 to separate the main vessel 600 and its branch vessels 620 from the surrounding tissue 630 while illuminating the main vessel 600 and its branch 620 with an illumination source 204 within the distal end 108 of the dissection tip 120. The process can also include capturing and transmitting an image signal, by an imaging device 204 located within the dissection tip 120, to a video processor 154 for displaying an image of the main vessel 600 and its branch vessels 620 to a user. The process can further include moving, using the image, a first cutting portion and a second cutting portion in a distal direction from a position proximally of the dissection tip 120 to capture a blood vessel 600 between the first and second cutting portions and capturing, using the image, a blood vessel 600 between the first cutting portion and the second cutting portion.

In some embodiments, the image signal can be transmitted over wiring extending internally through the elongated body 104 to a video processor 154 via a single cable 112. The single cable 112 can provide power for the cutting portion, the imaging device 204, and the illumination source 208 from a processing tower 150 and/or the image signal can be transmitted over wirelessly to a video processor 154 via a wireless transceiver 212 integrated on the circuit 200 within the distal tip 200.

It should be noted while preferred types of energy for various electrodes are indicated in the present disclosure, all electrodes can be energized using various sources of energy, including, but not limited to, resistive heating, ultrasound heating, and bipolar or monopolar RF energy. In some embodiments, the electrodes can be controlled independently of one another. It should also be noted that, when appropriate, the electrodes may be insulated with an insulating coating or insulating sheath.

Figure 7:
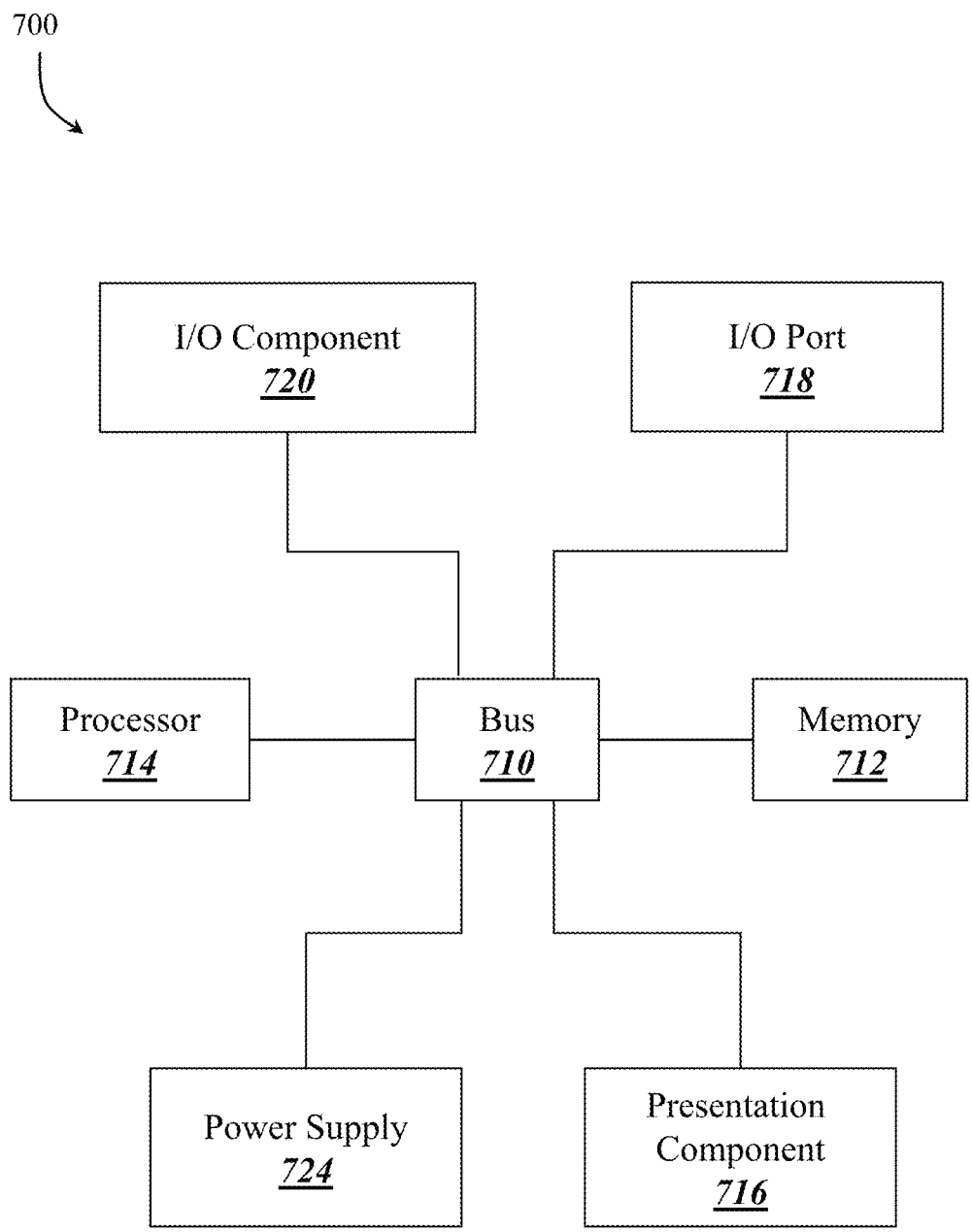
FIG. 7 is a diagrammatic illustration of a high-level architecture for implementing processes in accordance with aspects of the invention.

Any suitable computing device can be used to implement the computing devices 152, 154 and methods/functionality described herein and be converted to a specific system for performing the operations and features described herein through modification of hardware, software, and firmware, in a manner significantly more than mere execution of software on a generic computing device, as would be appreciated by those of skill in the art. One illustrative example of such a computing device 700 is depicted in FIG. 7. The computing device 700 is merely an illustrative example of a suitable computing environment and in no way limits the scope of the present invention. A "computing device," as represented by FIG. 7, can include a "workstation," a "server," a "laptop," a "desktop," a "hand-held device," a "mobile device," a "tablet computer," or other computing devices, as would be understood by those of skill in the art. Given that the computing device 700 is depicted for illustrative purposes, embodiments of the present invention may utilize any number of computing devices 700 in any number of different ways to implement a single embodiment of the present invention. Accordingly, embodiments of the present invention are not limited to a single computing device 700, as would be appreciated by one with skill in the art, nor are they limited to a single type of implementation or configuration of the example computing device 700.

The computing device 700 can include a bus 710 that can be coupled to one or more of the following illustrative components, directly or indirectly: a memory 712, one or more processors 714, one or more presentation components 716, input/output ports 718, input/output components 720, and a power supply 724. One of skill in the art will appreciate that the bus 710 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 7 is merely illustrative of an exemplary computing device that can be used to implement one or more embodiments of the present invention, and in no way limits the invention.

The computing device 700 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 700.

The memory 712 can include computer-storage media in the form of volatile and/or nonvolatile memory. The memory 712 may be removable, non-removable, or any combination thereof. Exemplary hardware devices are devices such as hard drives, solid-state memory, optical-disc drives, and the like. The computing device 700 can include one or more processors that read data from components such as the memory 712, the various I/O components 716, etc. Presentation component(s) 716 present data indications to a user or other device. Exemplary presentation components include a display device, speaker, printing component, vibrating component, etc.

The I/O ports 718 can enable the computing device 700 to be logically coupled to other devices, such as I/O components 720. Some of the I/O components 720 can be built into the computing device 700. Examples of such I/O components 720 include a microphone, joystick, recording device, game pad, satellite dish, scanner, printer, wireless device, networking device, and the like.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

As utilized herein, the terms "comprises" and "comprising" are intended to be construed as being inclusive, not exclusive. As utilized herein, the terms "example", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present disclosure will be apparent to those skilled in the art in view of the foregoing description. Accordingly, this description is to be construed as illustrative only and is for the purpose of teaching those skilled in the art the best mode for carrying out the present disclosure. Details of the structure may vary substantially without departing from the spirit of the present disclosure, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present disclosure be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A surgical device, comprising:
   an elongated body having disposed, at a distal end of the elongated body, a conical tip defining an inner cavity in fluid communication with the elongated body;

an imaging device coupled to the conical tip and designed to convert captured light into an image signal;

an illumination source at the distal end of the elongated body;

a cutting unit movable in a distal direction toward the conical tip; and a single cable connecting the imaging device to a processing tower remotely situated from the elongated body for providing data lines to the imaging device, wherein the single cable also provides power for the cutting unit, the imaging device, and the illumination source from the processing tower.

2. The surgical device of claim 1, wherein the cutting unit includes a first cutting portion and a second cutting portion for capturing a tissue segment between the first cutting portion and the second cutting portion.

3. The surgical device of claim 1, wherein the illumination source comprises at least one light emitting diode.

4. The surgical device of claim 1, wherein the imaging device is part of an integrated circuit, and wherein the integrated circuit further comprises a battery.

5. The surgical device of claim 1, wherein the imaging device is part of an integrated circuit, and wherein the integrated circuit further comprises a wireless transceiver.

6. The surgical device of claim 5, wherein the imaging device is configured to receive power from a battery of the integrated circuit and exchange data via the wireless transceiver.

7. The surgical device of claim 1, wherein the imaging device is part of an integrated circuit, and wherein the integrated circuit further comprises at least one of a conductive line and an optical line.

8. The surgical device of claim 7, wherein the conductive line comprises small gauge wiring extending from a housing of the surgical device, through the elongated body, and coupled to the imaging device.

9. The surgical device of claim 8, wherein the imaging device receives power and exchanges data over the small gauge wiring.

10. The surgical device of claim 1, wherein the surgical device is disposable.

11. A system, comprising:
a processing tower having an electrosurgical generator; and
a surgical device comprising:
an elongated body having disposed, at a distal end of the elongated body, a conical tip defining an inner cavity in fluid communication with the elongated body;
an imaging device coupled to the conical tip and designed to convert captured light into an image signal;
an illumination source at the distal end of the elongated body;
a cutting unit movable in a distal direction toward the conical tip; and
a single cable connecting the imaging device to the processing tower and through which the electrosurgical generator provides power to the imaging device, the cutting unit, and the illumination source.

12. The system of claim 11, wherein the processing tower further comprises a video processor for processing a signal received from the imaging device and a video monitor for displaying a video of the signal.

13. The system of claim 11, further comprising a wireless transceiver for transmitting signal data from the imaging device to the processing tower.

14. The system of claim 11, wherein the cutting unit includes a first cutting portion and a second cutting portion for capturing a tissue segment between the first cutting portion and the second cutting portion.

15. The system of claim 14, wherein the surgical device is disposable.

16. A method for harvesting a blood vessel, comprising:
advancing an elongated body having a dissection tip disposed at a distal tip of the elongated body along a tissue segment, the dissection tip having a cone shape defining an inner cavity, the cone shape being designed to minimize and prevent tearing or puncturing of surrounding tissue during its advancement along the tissue segment and the dissection tip having an imaging device located within the cavity such that the cavity remains in fluid communication with the elongated body;
illuminating the tissue segment with an illumination source;
capturing light and converting the captured light into an image signal and transmitting the image signal to a video processor for displaying an image of the tissue segment to a user;
moving, using the image, a first cutting portion and a second cutting portion in a distal direction from a position proximally of the dissection tip to capture the tissue segment between the first and second cutting portions; and
positioning, using the image, the tissue segment between the first cutting portion and the second cutting portion,
wherein a single cable provides power for the cutting portions, the imaging device, and the illumination source from a processing tower.

17. The method of claim 16, wherein the image signal is transmitted over wiring extending internally through the elongated body to the video processor via the single cable.

18. The method of claim 16, wherein the image signal is transmitted over wirelessly to the video processor via a wireless transceiver integrated within the distal tip.

19. A surgical device, comprising:
an elongated body having disposed, at a distal end of the elongated body, a conical tip defining an inner cavity in fluid communication with the elongated body;
an imaging device coupled to the conical tip and designed to capture light and convert the captured light into an image signal;
an illumination source at the distal end of the elongated body;
a cutting unit movable in a distal direction toward the conical tip; and
a single cable including a first channel for connecting the imaging device to a processing tower remotely situated from the elongated body for providing data lines to the imaging device, the single cable including at least a second channel for providing at least one of $CO_2$, saline, and other fluids, wherein the single cable also provides power for the cutting unit, the imaging device, and the illumination source from the processing tower.

20. A surgical device, comprising:
an elongated body having disposed, at a distal end of the elongated body, a conical tip defining an inner cavity in fluid communication with the elongated body;
an imaging device coupled to the conical tip and designed to capture light and convert the captured light into an image signal;
an illumination source at the distal end of the elongated body;
a cutting unit movable in a distal direction toward the conical tip; and a single cable connecting the imaging device to a processing tower remotely situated from the elongated body, wherein the single cable includes a communication circuitry designed to transmit the image signal from the imaging device to an external display in the processing tower, and wherein the single cable also provides power for the cutting unit, the imaging device, and the illumination source from the processing tower.

\* \* \* \* \*